United States Patent
Rogacs et al.

(10) Patent No.: US 10,871,481 B2
(45) Date of Patent: Dec. 22, 2020

(54) SENSORS FOR COOLING SYSTEM FLUID ATTRIBUTES

(71) Applicant: Hewlett Packard Enterprise Development LP, Houston, TX (US)

(72) Inventors: Anita Rogacs, Palo Alto, CA (US); Greg Scott Long, Corvallis, OR (US); Tahir Cader, Liberty Lake, WA (US); Keith Mathew McAuliffe, Houston, TX (US); John Franz, Houston, TX (US)

(73) Assignee: Hewlett Packard Enterprise Development LP, Houston, TX (US)

( * ) Notice: Subject to any disclaimer, the term of this patent is extended or adjusted under 35 U.S.C. 154(b) by 126 days.

(21) Appl. No.: 15/546,090

(22) PCT Filed: Jan. 30, 2015

(86) PCT No.: PCT/US2015/013986
§ 371 (c)(1),
(2) Date: Jul. 25, 2017

(87) PCT Pub. No.: WO2016/122667
PCT Pub. Date: Aug. 4, 2016

(65) Prior Publication Data
US 2018/0017538 A1    Jan. 18, 2018

(51) Int. Cl.
*G01N 33/18*    (2006.01)
*G01N 27/02*    (2006.01)
(Continued)

(52) U.S. Cl.
CPC .......... *G01N 33/1886* (2013.01); *F01P 11/14* (2013.01); *F01P 11/18* (2013.01);
(Continued)

(58) Field of Classification Search
None
See application file for complete search history.

(56) References Cited

U.S. PATENT DOCUMENTS

| 4,338,959 A | 7/1982 | Krueger et al. |
| 4,745,760 A * | 5/1988 | Porter ............... F17C 3/085 62/50.2 |

(Continued)

FOREIGN PATENT DOCUMENTS

| CN | 101472940 A | 7/2009 |
| CN | 103917863 A | 7/2014 |

(Continued)

OTHER PUBLICATIONS

International Search Report and Written Opinion received for PCT Patent Application No. PCT/US2015/013986, dated Oct. 19, 2015, 11 pages.

(Continued)

*Primary Examiner* — Richard C Gurtowski
(74) *Attorney, Agent, or Firm* — Hewlett Packard Enterprise Patent Department (57) ABSTRACT

An example device in accordance with an aspect of the present disclosure includes a sensor, a controller, and an injector. The sensor is to provide sensor output regarding fluid chemistry of a fluid of a cooling system. The controller is to identify attributes of the fluid. The injector is to inject at least one additive into the fluid to bring at least one attribute into a threshold range.

20 Claims, 5 Drawing Sheets

(51) Int. Cl.
*F01P 11/14* (2006.01)
*F01P 11/18* (2006.01)
*H05K 7/20* (2006.01)
*F01P 3/00* (2006.01)
*G01N 27/07* (2006.01)
*G01N 27/407* (2006.01)

(52) U.S. Cl.
CPC ....... *G01N 27/026* (2013.01); *H05K 7/20672* (2013.01); *F01P 2003/001* (2013.01); *F01P 2025/80* (2013.01); *G01N 27/07* (2013.01); *G01N 27/4071* (2013.01)

(56) References Cited

U.S. PATENT DOCUMENTS

| | | | |
|---|---|---|---|
| 6,278,281 | B1 | 8/2001 | Bauer et al. |
| 6,861,851 | B2 | 3/2005 | Lvovich et al. |
| 7,109,729 | B2 | 9/2006 | Schilowitz et al. |
| 7,570,058 | B1 * | 8/2009 | Wong ................. G01R 33/3856 324/318 |
| 2004/0055317 | A1 | 3/2004 | Nomura et al. |
| 2007/0193285 | A1 * | 8/2007 | Knight .................... F25B 43/04 62/126 |
| 2008/0020470 | A1 | 1/2008 | Keister |
| 2013/0284597 | A1 | 10/2013 | Ren et al. |
| 2014/0326340 | A1 | 11/2014 | Kuriki et al. |

FOREIGN PATENT DOCUMENTS

| | | |
|---|---|---|
| DE | 102005043699 A1 | 3/2007 |
| EP | 2469197 | 6/2012 |
| EP | 3250913 A1 | 12/2017 |
| JP | H051541 | 1/1993 |
| JP | 2008-008750 A | 1/2008 |
| WO | WO-020733 A1 | 4/2000 |
| WO | WO-031056304 A1 | 7/2003 |
| WO | 2016/122667 A1 | 8/2016 |

OTHER PUBLICATIONS

International Preliminary Report on Patentability received for PCT Patent Application No. PCT/US2015/013986, dated Aug. 10, 2017, 10 pages.

European Search Report and Search Opinion Received for EP Application No. 15880557.2, dated Jan. 15, 2018, 8 pages.

Charles T. Johnson, "The Control of pH and Oxidation Reduction Potential (ORP) in Cooling Tower Applications," Feb. 20, 2007, pp. 1-6, Walchem Corporation.

H. Ashassi-Sorkhabi et al., "Effects of Solution Hydrodynamics on Corrosion Inhibition of Steel by Citric Acid in Cooling Water," Journal of Materials Engineering and Performance, Aug. 2014, pp. 2992-3000, vol. 23(8).

Zhang Hong Liang et al., "Corrosion On-line Monitoring Technology of Circulation Cooling Water System," Dec. 12, 2011, pp. 1-3, IEEE.

\* cited by examiner

SENSORS FOR COOLING SYSTEM FLUID ATTRIBUTES

BACKGROUND

Liquid-cooled environments may involve complex water chemistry to protect a system's wetted materials. However, fluid chemistry monitoring and/or provisioning can be labor-intensive, expensive, and highly visible and potentially disruptive to the customer.

DETAILED DESCRIPTION

Fluid in liquid-cooled systems is to be maintained in a proper chemical composition to avoid corroded metals, leaks, and biological particulates that can clog fluid passages and filters. Commercial solutions to monitor and maintain chemistry are expensive, need separate instrumentation to separately monitor different chemicals, and rely on human intervention.

A given liquid-cooled environment may involve various wetted materials exposed to the liquid, imposing difficulties on balancing a chemical composition of the liquid. Compatibility of the liquid with the wetted materials can address corrosion and other issues that may risk shutdown of a liquid-cooled deployment. Examples described herein may involve liquid mixtures of chemicals including corrosion inhibitors, multiple different biocides, and pH buffers. The balanced chemistry of the liquid may be perturbed by, for example, the replacement and/or addition of equipment sharing the liquid (e.g., adding a computing system rack). Subsequently, it may be challenging to perform an intensive procedure of manually monitoring and adjusting fluid chemistry until the new mixture stabilizes. Accordingly, there is a need to improve the cooling fluid's chemical stability and accuracy of chemical mixtures, and to reduce service costs and/or automate the aspect of adjusting the liquid cooling chemical protection.

Examples described herein enable real-time chemistry monitoring, quantification of, and provisioning of supplies for liquid-cooled platforms. Examples also may perform real-time re-balancing of the fluid chemistry, to counteract the fluid from becoming unbalanced. Furthermore, examples may automatically provision additives or chemicals that are running low, to avoid running out. Thus, significant cost savings and greater accuracy may be enjoyed, while improving convenience and reducing a need for manual intervention.

Figure 1:
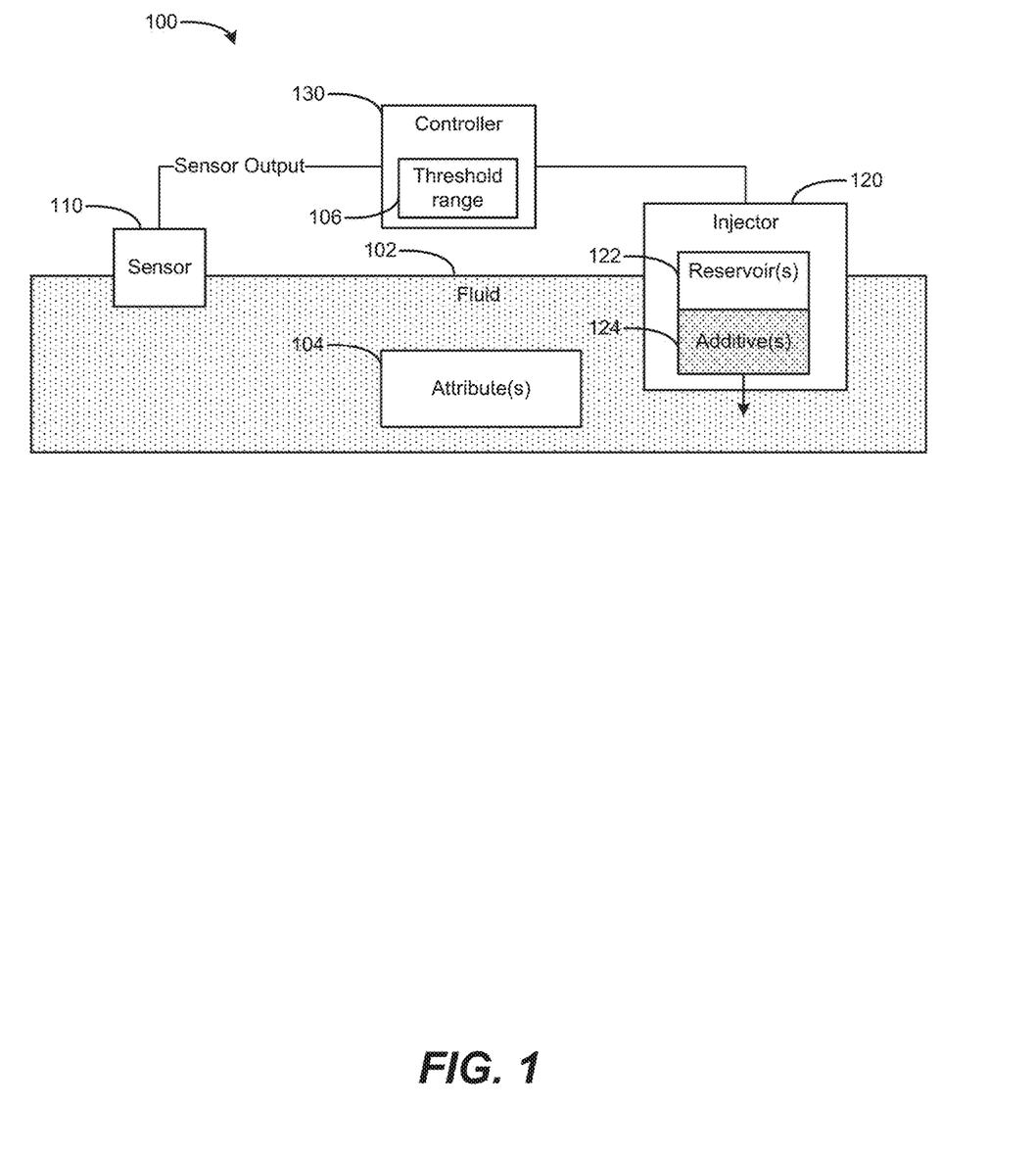
FIG. 1 is a block diagram of a device including a sensor, an injector, and a controller according to an example.

FIG. 1 is a block diagram of a device 100 including a sensor 110, an injector 120, and a controller 130 according to an example. The sensor 110 is coupled to fluid 102. The controller 130 is to receive sensor output from the sensor 110, and identify whether at least one attribute 104 of the fluid 102 is within a corresponding at least one threshold range 106. The controller 130 is to direct the injector 120 to inject at least one additive 124 from a corresponding at least one reservoir 122 into the fluid 102.

The device 100 may be coupled to a given liquid-cooled system, e.g., to a computing rack having a liquid cooling loop of fluid 102 circulating through the rack. Other applications include computing systems, computing racks, computing servers, datacenters, including Performance Optimized Datacenters (PODs), and other applications to which liquid-cooling solutions may be applied. In alternate examples, the device 100 may be coupled to fluid 102 where access to the fluid 102 is available, e.g., at a floor-mounted reservoir, a radiator, a pump, a Coolant Distribution Unit (CDU), or elsewhere. A CDU is to control the flow of fluid to computing racks, for example, and may receive sensors 110, additives 124 and other chemicals, along with supporting hardware such as controller 130. Example device 100 may be compatible with platforms having various different wetted materials lists, such as those including different grades of aluminum, copper, stainless steel, cast iron, brass, and so on used in a liquid-cooling loop and the computing system in which the fluid circulates. Such metals, and other non-metallic materials, may be associated with a particular susceptibility to corrosion when immersed in fluids at high temperatures (e.g., the environment of a liquid-cooling system). Accordingly, a given fluid may include a complex chemical mix to protect the various metals and other materials from corrosion, such as pH stabilizers, corrosion inhibitors, biocides, and the like.

Device 100 may identify and/or adjust the attributes 104 of the fluid 102, such as what levels of various additives 124 are contained in the fluid 102. The fluid 102 may be a pre-mix solution that is initially balanced for application to a given liquid-cooling platform and/or computing system. Alternatively, the fluid 102 may be off-the-shelf liquid coolant or even untreated water, to which various additives 124 may be added by injector 120 to balance the fluid 102 for use by a given system. The fluid 102 may be monitored over time for any changes or deviations from a desired chemical balance appropriate for a given application. Maintaining a given attribute 104, such as pH, can be challenging in a computing environment given the manner in which, e.g., a server cluster may be used. For example, a given rack, CDU, or other component in the fluid circulation loop may be removed from operation for servicing and/or replaced with a new component containing a different composition of coolant fluid. A given system may experience a fluid leak that the user replaces with tap water. Such modifications may substantially change the chemical mix, causing a need for chemicals to be re-balanced. Rather than needing expensive and time consuming manual adjustment by a service professional, examples described herein may identify the attributes 104 of the fluid 102 using the sensor 110, to inject appropriate additives 124. Such information may be monitored in real-time by controller 130 for real-time adjustment by injector 120, and reported back to a remote location in case further action is warranted (e.g., ordering replacement additives 124, raising an alert due to anomalous behavior, etc.).

The device 100 may use sensor 110 to identify a plurality of attributes 104. Various types of sensors may be used, including an impedance sensor 110 to obtain sensor output to be used for, e.g., a dielectric measurement of the fluid 102. For example, dielectric attributes may be derived from an impedance profile of the fluid 102, including permittivity, phase, and other utilitarian attributes 104. The sensor 110 may be a chemical sensor for use with Electrochemical Impedance Spectroscopy (EIS), Because a single sensor 110 may be used to discern multiple different attributes 104 of the fluid 102, device 100 may be compact and readily integrated into a CDU or other portion of a liquid-cooling platform, to conduct in-situ and real-time measurement of the fluid 102 attributes 104. The sensor 110 may enable EIS to be used to measure an alternating current (AC) complex electrical impedance of the fluid, between two or more electrodes placed in the fluid 102 at a desired location such as a fluid-carrying tube. In an example, a controlled AC voltage may be applied across electrodes of the sensor 110, and a magnitude of the resultant current, and a phase difference between the current and the voltage waveforms, allows for determination of the real and imaginary components of the impedance across the fluid 102. In alternate examples, a controlled current may be passed into the fluid 102 (e.g., using an additional sensor 110 not shown in FIG. 1), and the resulting voltage magnitude and phase across two electrodes of the sensor 110 may be measured.

The sensor 110 may be directed (e.g., by controller 130) to sense attributes 104 at various intervals and/or constantly monitor the attributes 104. The sensor 110 may be directed to take active readings by constantly pinging. Alternatively, the sensor 110 may be directed to ping at a certain rate/frequency according to system needs (e.g., to conserve energy/resources), such as in response to system modifications. The sensor 110 may obtain measurements of attributes 104 across many different electrical frequencies, to form, e.g., a spectrum vector of frequency-impedance pairs. The controller 130 may compare the measured spectrum to pre-determined baseline spectra (e.g., for fresh fluid 102 including all applicable additives/chemicals mixed in). Thus, the spectrum of sensor output so obtained may be used to determine whether the attributes 104 such as pH, biocide levels, and/or corrosion inhibitor levels are all within desired specifications.

The injector 120 may be directed by the controller 130 to inject additives 124 from corresponding reservoirs 122 into the fluid 102. For example, the controller 130 may determine that levels of a given attribute 104 have fallen outside of a threshold range 106, and direct the injector 120 to inject a corresponding additive 124 to bring the attribute 104 into the desired threshold range 106. The injector 120 may use various types of injection technologies, such as microfluidic delivery or other technologies. In an example, the injector 120 may use inkjet technology to inject the additives 124. In alternate examples, the injector 120 may be based on a Thermal Ink Picojet System (TIPS) technology to inject highly controlled volumes of additives 124 into the circulating fluid 102. The injector 120 may include a pump (not specifically illustrated) and may be calibrated to overcome any backpressure introduced by the fluid 102, if applicable.

The reservoir(s) 122 may include at least one reservoir 122 to contain a corresponding at least one additive 124. The reservoirs may be formed as a portion of the device 100 to receive additives 124. In an example, the reservoirs 122 may be refillable. In alternate examples, the reservoirs 122 may be formed as disposable cartridges similar to inkjet cartridges. The reservoirs 122 may be used to store various different chemicals used to balance fluid chemistry attributes 104 according to a given application. The controller 130 may direct the injector 120 to inject any or all of the various additives 124, including pH buffers, corrosion inhibitors, and/or biocides. Such directions may be given in real-time, e.g., in response to the fluid chemistry as indicated by attributes 104 getting out-of-balance (e.g., as a result of a rack replacement, a CDU servicing event, a leak followed by the addition of water, etc.) or otherwise falling outside of corresponding threshold range(s) 106.

The reservoirs 122 also may include gauges or other appropriate technology to monitor levels of additives 124. In an example, a two-electrode gas gauge capacitive sensor (SHAID sensor used in print heads) may be used to monitor the various levels of additives 124 in their various corresponding reservoirs 122.

The reservoirs 122 may be based on a removable modular implementation, such as a removable cartridge(s). In an example, a removable cartridge may be provided for a given additive 124. In an alternate example, a removable cartridge may be provided to store a plurality of additives 124. Accordingly, the additives 124 may easily be replaced without a need to break open the cooling fluid loop to manually pour in the various additive(s) 124 and manually reinstall the loop (associated with risk of fluid leaks). An end user may easily, without formal training, obtain a modular refill for the reservoir(s) 122, couple it to the device 100, and continue computing system operations without a need to halt server operations. Accordingly, the reservoirs 122 of additives 124 may be easily and quickly replenished similarly to other computing consumables such as ink cartridges or toner.

Controller 130 may electrically interface with the sensor 110 and injector 120, and may be provided as a low-cost solution, such as a proportional-integral-derivative (PID) or other control system, a processor, a system on chip (SoC), an application-specific integrated circuit (ASIC), and so on. The controller 130 may include storage (not specifically illustrated) to store various values and/or tables corresponding to threshold ranges 106 and behaviors of various fluids 102 and additives 124. If the controller 130 identifies that attribute(s) 104 are out of balance (e.g., as a result of a rack removal/replacement, a leak followed by the addition of water, etc.), the controller 130 may direct controlled amounts of the additives 124 (pH buffers, corrosion inhibitors, biocides, etc.) to be added to the fluid 102 to re-balance the fluid chemistry. The controller may monitor the state of the overall cooling platform in real-time via the sensor 110 (and/or other sensor, or couplings to other controllers of other systems), and direct the injector 120 to slow or terminate injections of corresponding additive(s) 124 as desired chemical levels of attribute(s) 104 are obtained. The process may be repeated as desired.

The controller 130 may be associated with threshold range(s) 106, which may correspond to a given attribute 104 and/or additive 124. For example, a threshold range 106 may be provided for identifying when an attribute 104 exits the range at which time the corresponding additive 124 should be added to rebalance that attribute 104 and bring it back into that threshold range. Similarly, threshold ranges may be used to identify when attributes 104 have entered a condition to be remedied (e.g., a first desirable take-no-action threshold, a second no-action threshold, and a third take-action threshold). A threshold range 106 can be established based on various techniques, such as volume-based calculations, field tests, laboratory tests, and so on, to independently determine various ranges within which the attributes 104 should remain to correspond to balanced fluid chemistry. The various components of device 100, such as sensor 110 and injector 120, may be calibrated according to those determined levels. The controller 130 may then monitor sensor 110 to identify whether the monitored sensor output indicates that an attribute has reached a certain threshold range 106. If so, the controller 130 may direct the injector 120 to inject the corresponding additive(s) 124 accordingly. The controller 130 may be preset with and/or store various threshold ranges 106 corresponding to given fluids and additives. Such threshold ranges 106 may be customized according to field conditions or situations that may arise in a particular application.

The controller 130 may include various and multiple threshold ranges 106. In addition to identifying when to add more additives 124, the threshold ranges 106 may be used to identify whether the device 100 is behaving inconsistent with normal operation. For example, a given attribute 104 may remain at an undesirable value despite injection of corresponding additive 124 (that would normally bring the attribute 104 back into balance). Accordingly, the controller 130 may generate a service call indication, to alert a user to manually inspect the device 100 for proper operation (e.g., identify whether the fluid 102 has a leak in the system, or that a CDU is improperly auto-filling the cooling fluid loop with water when not needed, and so on). Thus, the controller 130 can expediently identify and bring attention to more serious issues that may arise in a liquid-cooling platform, which might otherwise go unnoticed. The threshold range(s) 106 not only may correspond to the attributes 104 of the fluid 102, but also may correspond to characteristics of the reservoirs 122 and/or additives 124. For example, controller 130 may identify attributes regarding a fill level of the reservoir(s) 122, and whether components are mechanically functioning properly, etc.

Device 100 also may therefore monitor status of the additives 124. For example, controller 130 may identify that a given additive 124 is running low, and provision replacement additives 124 to be ordered. For example, the controller 130 may identify that a level of any of the additives 124 has reached a pre-determined action level, and issue a signal to notify the user and/or automatically order refill additive(s) 124. For example, the signal may be communicated to a pre-existing communication network to automatically order more additives from a supply chain. The signal also may be used to inform the user to schedule the replacement/refilling/servicing of the corresponding additive reservoir 122. Accordingly, device 100 may anticipate future needs of a system, ensuring that the correct additives 124 are always in stock on site to avoid any downtimes. Furthermore, device 100 may schedule preventative maintenance when most convenient to a customer, e.g., during scheduled down times, to avoid affecting the customer's operations.

Example devices 100 may be based on sensor/circuit hardware that may be relatively low in costs (e.g., particularly when compared against the cost of service contracts). Device 100 enables highly automated treatment of fluid 102, that controllably enables repeatable water chemistry, increased reliability, reduced service and warranty costs, and an overall better customer experience. Furthermore, because device 100 can react so quickly to changes in chemistry of the fluid 102 to re-balance various attributes 104 of the fluid chemistry, a given liquid-cooling application fitted with device 100 will continuously experience lower corrosive stresses over its entire lifetime, thereby extending overall operational lifetime and improving cooling efficiencies. Device 100 also enables fluid chemistry information to be much more transparent to the customer, significantly reducing the inconvenience of a need to manually rebalance the fluid chemistry every time a customer adjusts a rack, CDU, water wall, or other component that would otherwise affect the cooling fluid loop. Furthermore, any issues in the cooling loop may be identified early, such as a leak or other misconfiguration, to catch any problems early and preventing more serious resulting damage from arising.

Figure 2:
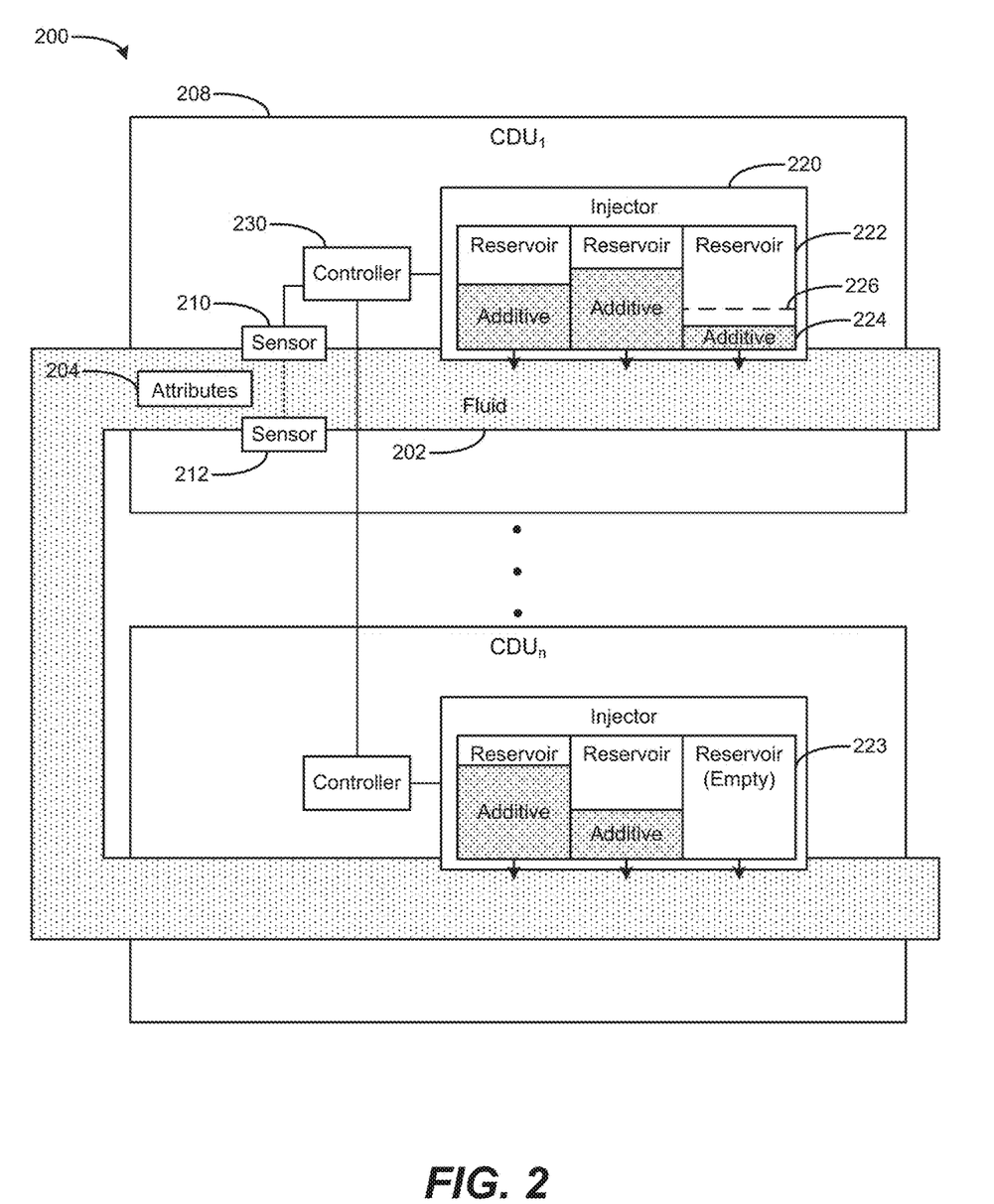
FIG. 2 is a block diagram of a system including a plurality of coolant distribution units (CDUs) according to an example.

FIG. 2 is a block diagram of a system 200 including a plurality of coolant distribution units 208 ($CDU_1 \ldots CDU_n$) according to an example. A CDU 208 includes sensor components 210, 212, an injector 220, and a controller 230 according to an example. The controller 230 may be coupled to other controllers of other CDUs, to coordinate operations between the plurality of CDUs. The sensor 210, 212 is coupled to fluid 202 to provide sensor output to the controller 230 regarding attributes 204 of the fluid 202. The controller 230 is to direct the injector 220 to inject additives 224 from reservoirs 222 into the fluid 202. A reservoir 222 and additive 224 may include an action level 226, e.g., to identify when the additive 224 needs refilling. Reservoir 223 of $CDU_n$ is shown as empty.

System 200 illustrates a liquid-cooling deployment including more than one CDU 208. For example, a set of two CDUs 208 may be used to support four to six computing racks. The plurality of CDUs 208 may provide a plurality of sources of additives 224 for a given fluid 202 (e.g., because the CDUs 208 may share the same column manifolds in a given installation, fluidically coupled to the same cooling fluid loop). Accordingly, additional additives are available, both in terms of total quantify and delivery rate. The controllers 230 of different CDUs 208 may communicate with each other, e.g., in a shared/distributed, master/slave, or other arrangement. For example, a master CDU 208 may identify which CDU 208 should dispense a given additive, or which should identify a given attribute 204, and so on. In an example, controller 230 of $CDU_1$ may direct its injector to dispense extra fluid, to compensate for the empty reservoir 223 of $CDU_n$. Similarly, the controllers 230 may direct the injectors 220 to decrease injections of additives 224 contained at multiple CDUs 208, to spread the injection across an entire system and minimize instances of running out of a given additive 224 at a given CDU 208. Injector 220 illustrates three different reservoirs 222 containing three different respective additives 224, such as a biocide, a pH buffer, and a corrosion inhibitor. The reservoirs 222 may each be provided as a replaceable cartridge, and in alternate examples, a single cartridge may be provided, containing three internal reservoirs 222 and corresponding additives 224.

In an example, components illustrated in CDU 208 may be retrofitted in the field, adapted to plug-in to an existing CDU 208. In alternate examples, the various components may be adapted to be mounted onto existing hardware exposed to fluid 202 elsewhere in a computing system, such as a fluid reservoir.

The sensor 210, 212 is shown at least partially immersed in the fluid 202 of the CDU 208, and electrically coupled to the CDU 208 (e.g., via the controller 230. The sensor 210, 212 is shown having multiple components. In an example, the sensor 210, 212 may represent dual pins of a pin-type electrode geometry (e.g., provided as a 2-prong fork), With such a geometry, both probes of the sensor 210, 212 may be inserted into the fluid 202, without a need to substantially modify the system 200 (e.g., to accommodate relatively larger plates of a plate-based sensor). Accordingly, such sensors 210, 212 are relatively more versatile and compact, and may be placed in additional locations with more placement options, including placement of a plurality of sensors 210, 212 throughout a given system 200.

Figure 3:
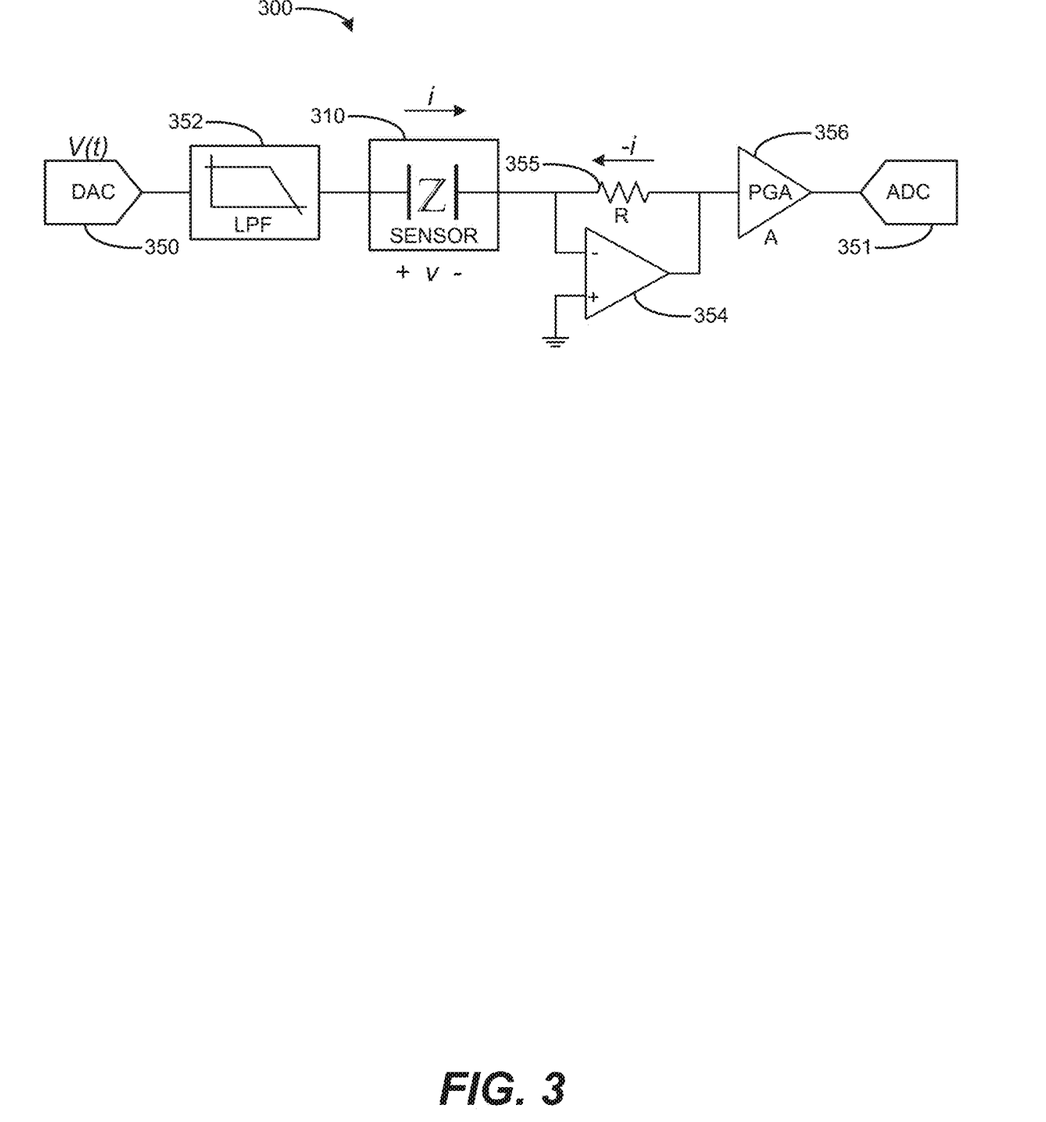
FIG. 3 is a block diagram of a device including a sensor according to an example.

FIG. 3 is a block diagram of a device 300 including a sensor 310 according to an example. The device 300 also includes a digital-to-analog converter (DAC) 350, a lowpass filter 352, an operational amplifier 354 and resistor 355, a proportional gain amplifier (PGA) 356, and an analog-to-digital converter 351. In an example, the device 300 may serve as controller 130 and sensor 110 of FIG. 1. The device 300 may be implemented as a proportional-integral-derivative (PID) controller, providing a control loop feedback mechanism.

Notably, the device 300 may rely on a single sensor 310 to enable Electrochemical Impedance Spectroscopy (EIS), based on reliably generating the corresponding AC signals to allow for collecting sensor output and ping-back of the imaginary component of the impedance generated across the sensor 310. In alternate examples, multiple sensors may be deployed to achieve N+1, N+2, 2N, and other redundancy modes of operation.

In operation, the sensor 310 is to generate and apply a small AC signal, propagated across the electrodes of the sensor 310 and through the fluid. In response, the fluid will be perturbed by the applied signal and change the resultant waveform across the electrodes of the sensor 310 (e.g., change its amplitude and phase to give rise to an impedance profile). The op amp 354 may then sense the output current i from the sensor 310, and the proportional gain amplifier (PGA) 356 may sense the phase difference between the applied signal(s) and the measured signal(s) (e.g., a sensed sine wave altered in phase relative to the originally applied input sine wave).

Thus, a very weak AC signal may be applied across the electrodes of the sensor 310, to generate the resultant current. The phase relationship between the applied potential and the generated current, i.e., the lag between, e.g., application of current and generation of current. This relationship may be identified (e.g., by a controller) as a function of frequency, to obtain a spectral response providing total impedance as a function of frequency. The total impedance may be broken down into components mathematically, to reveal physical phenomenon occurring in the fluid under analysis (e.g., components corresponding to given attributes affected by additives). Accordingly, by observing particular components of the total impedance as a function of frequency, device 300 may identify attributes such as pH and how the attributes fall out of a threshold range, and then restore balance to the attributes to bring them back within the threshold based on additive injections.

Device 300 thus may provide electrical signal generation and current (i) and voltage (v) measurements. Multiple sensing tasks may be achieved using a single sensor 310, without a need to install multiple different sensors to identify a plurality of attributes of a given fluid (such as different additive levels in the fluid). Device 300 may use impedance spectroscopy to identify a breadth of attributes within a given range of sensing. For example, device 300 may apply a single type of frequency sweep across the sensor 310, to identify various monitored attributes (e.g., pH, biocide, corrosion inhibitor) that resolve within the frequency space corresponding to the frequency sweep of a single scan. Various attribute responses may be characterized/benchmarked to identify what is occurring in the frequency space/sweep/range.

Figure 4:
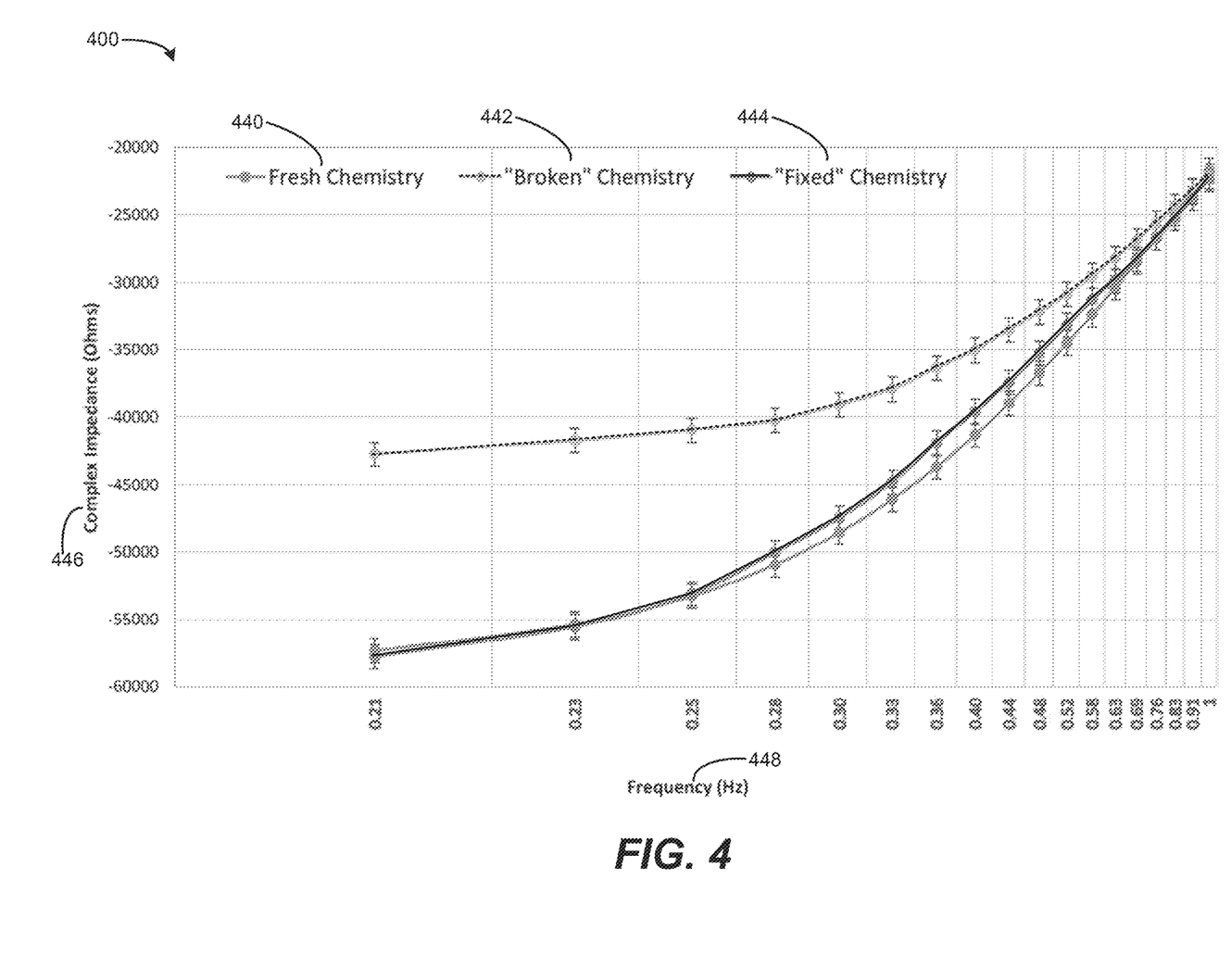
FIG. 4 is a chart of fluid chemistry based on complex impedance vs frequency according to an example.

FIG. 4 is a chart 400 of fluid chemistry 440, 442, 444 based on complex impedance 446 vs frequency 448 according to an example. The complex impedance 446 may involve an imaginary portion/component of the dielectric impedance waveform of a cooling fluid of a computing server. Measurements such as those in FIG. 4 may be performed at many different electrical frequencies 448, to form a spectrum vector of frequency-impedance pairs. Accordingly, examples described herein may compare (e.g., by a controller) the measured spectrum vector to pre-determined baseline spectra (e.g., for fresh fluid containing relevant chemical additives premixed). Such comparison may be used to determine whether the various fluid attributes, such as pH, biocide levels, and corrosion inhibitor levels, are within specifications, and whether additive injections are needed (and what amount of additive would be appropriate).

In the illustrated example of FIG. 4, the pH level of fluid chemistry for a given computing system (Fresh Chemistry 440) is perturbed by a direct spike with dilute acid (to achieve the "Broken" Chemistry 442). The perturbation is followed by restoration to nominal levels ("Fixed" Chemistry 444) by subsequent direct injection with dilute alkaline solution. Accordingly, loss of pH control and restoration to pre-injection baseline conditions is readily detectable by the present examples, which may use real-time impedance monitoring. A similar approach may be accomplished for corrosion inhibitor and biocide levels (or other attributes) in a cooling solution, to achieve actionable levels following direct injection of appropriate additive chemistry to restore the fluid solution to proper concentration levels. Thus, it is possible to quantify and restore fluid chemistry of multiple attributes using the impedance approach with a single chemical sensor.

Figure 5:
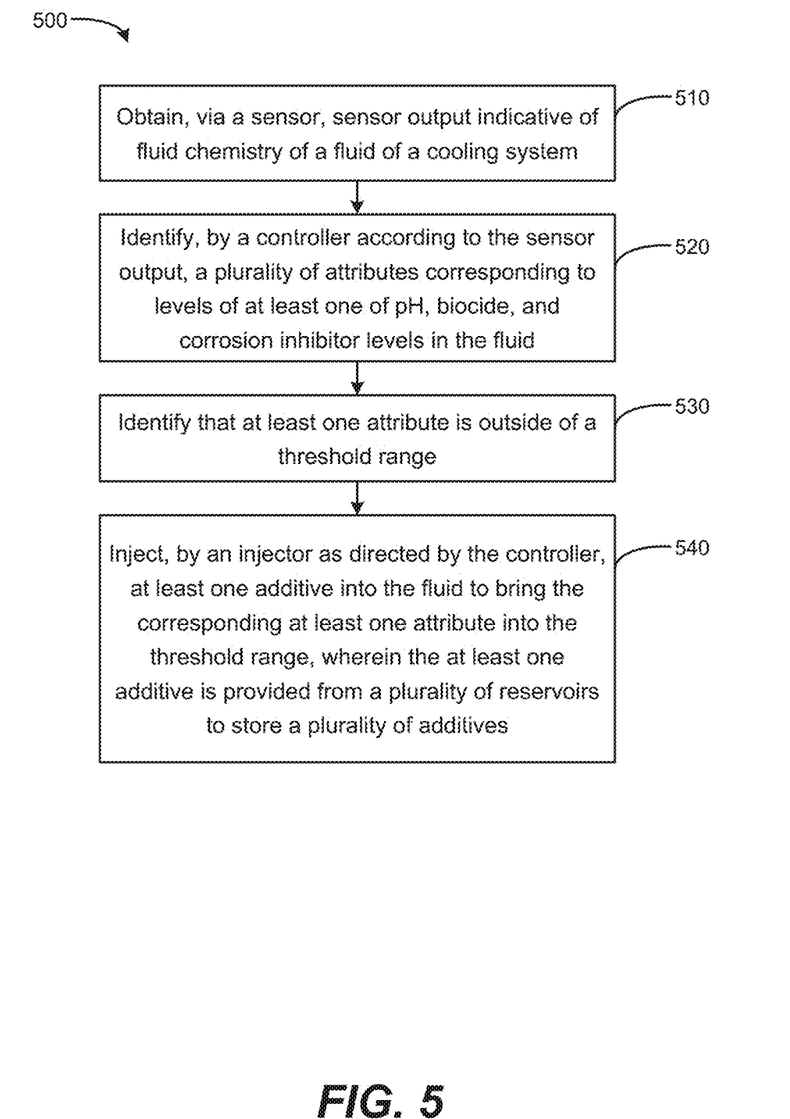
FIG. 5 is a flow chart based on identifying fluid attributes according to an example.

Referring to FIG. 5, a flow diagram is illustrated in accordance with various examples of the present disclosure. The flow diagram represents processes that may be utilized in conjunction with various systems and devices as discussed with reference to the preceding figures. While illustrated in a particular order, the disclosure is not intended to be so limited. Rather, it is expressly contemplated that various processes may occur in different orders and/or simultaneously with other processes than those illustrated.

FIG. 5 is a flow chart 500 based on identifying fluid attributes according to an example. In block 510, sensor output indicative of fluid chemistry of a fluid of a cooling system is obtained via a sensor. For example, a controller may receive sensor output from a single sensor in response to a frequency sweep applied to the single sensor that is exposed to cooling fluid. In block 520, a controller is to identify, according to the sensor output, a plurality of attributes corresponding to levels of at least one of pH, biocide, and corrosion inhibitor levels in the fluid. For example, a single sensor may identify two or more attributes indicating a health of the chemistry of the fluid. In block 530, at least one attribute is identified as being outside of a threshold range. For example, the single sensor may identify that levels of pH are undesirably high, and that levels of biocide are undesirably low. In block 540, an injector is to inject, as directed by the controller, at least one additive into the fluid to bring the corresponding at least one attribute into the threshold range. For example, the controller may direct the injector to inject an incremental amount, check the sensor, and repeat until the desired attribute range is achieved. The at least one additive is provided from a plurality of reservoirs to store a plurality of additives. For example, an injector may be adapted to receive a user-replaceable cartridge containing a plurality of additives in a plurality of reservoirs. Thus, a user may replenish the additives without a need for an expensive service call.

Examples provided herein may be implemented in hardware, software, or a combination of both. Example systems can include a processor and memory resources for executing instructions stored in a tangible non-transitory medium (e.g., volatile memory, non-volatile memory, and/or computer readable media). Non-transitory computer-readable medium can be tangible and have computer-readable instructions stored thereon that are executable by a processor to implement examples according to the present disclosure.

An example system (e.g., a computing device) can include and/or receive a tangible non-transitory computer-readable medium storing a set of computer-readable instructions (e.g., software), As used herein, the processor can include one or a plurality of processors such as in a parallel processing system. The memory can include memory addressable by the processor for execution of computer readable instructions. The computer readable medium can include volatile and/or non-volatile memory such as a random access memory ("RAM"), magnetic memory such as a hard disk, floppy disk, and/or tape memory, a solid state drive ("SSD"), flash memory, phase change memory, and so on.

What is claimed is:

1. A device comprising:
   a sensor to provide sensor output regarding fluid chemistry of a fluid of a cooling system, the cooling system comprising a liquid cooling loop disposed in a computer system;
   an injector to inject at least one additive into the fluid, the injector including a plurality of reservoirs to store a plurality of additives wherein at least one of the plurality of reservoirs is replenishable with the at least one additive without stopping the computer system;
   a controller to:
     identify based on the sensor output, a plurality of attributes corresponding to at least one of pH, biocide, and corrosion inhibitor levels of the fluid;
     identify that at least one attribute is outside of a threshold range;
     direct the injector to inject the at least one additive corresponding to the at least one attribute, to bring the at least one attribute into the threshold range; and
     send an order to a remote location for at least one replacement additive when the at least one additive reaches an action threshold fill level.

2. The device of claim 1, wherein sensor is a chemical sensor based on Electrochemical Impedance Spectroscopy (EIS) to identify changes to the attributes in real-time.

3. The device of claim 1, wherein the controller is to: identify the plurality of attributes in real-time, and direct the injector to inject the at least one additive into the fluid in real-time.

4. The device of claim 1, wherein the controller is to identify the plurality of attributes based on a complex impedance of a frequency response of the sensor output, including real and imaginary components.

5. The device of claim 1, wherein the controller is to identify the plurality of attributes based on a spectrum vector of frequency-impedance pairs.

6. The device of claim 1, wherein the sensor is to identify a dielectric measurement of the fluid.

7. The device of claim 1, wherein the sensor is based on pin electrodes.

8. The device of claim 1, wherein the controller is to identify whether a fill level of a given reservoir has reached an action threshold, and generate an action signal in response to reaching the action threshold.

9. A system comprising:
   a coolant distribution unit (CDU) to distribute a fluid of a cooling system and control a flow of the fluid to a computing rack;
   a sensor coupled to the CDU to provide sensor output;
   a controller to identify in real-time, based on the sensor output, a plurality of attributes of fluid chemistry of the fluid;
   an injector to inject in real-time at least one additive into the fluid, wherein the injector includes a plurality of reservoirs to store a plurality of additives, and a corresponding plurality of gauges to identify fill levels of the plurality of reservoirs; and
   the controller to identify, based on the sensor output, that at least one attribute is outside of a threshold range, direct the injector to inject a corresponding at least one additive to bring the at least one attribute into the threshold range, wherein the controller is to identify that a given reservoir fill level has reached an action threshold, and provide a refill indication corresponding to the given reservoir, and send an order to a remote location for at least one replacement additive when the at least one additive reaches an action threshold fill level.

10. The system of claim 9, further comprising a plurality of CDUs to distribute the fluid throughout the cooling system, wherein controllers of different CDUs are in communication to coordinate injections of additives into the fluid to cooperatively bring a given attribute into a corresponding threshold range.

11. A method, comprising:
    obtaining, via a sensor, sensor output indicative of fluid chemistry of a fluid of a cooling system;
    identifying, by a controller according to the sensor output, a plurality of attributes corresponding to levels of a pH, a biocide, and a corrosion inhibitor in the fluid;
    identifying that at least one attribute is outside of a threshold range; and
    injecting, by an injector as directed by the controller, at least one additive into the fluid to bring the corresponding at least one attribute into the threshold range, wherein the at least one additive is provided from a plurality of reservoirs to store a plurality of additives and;
    provisioning by automatically ordering from a remote location at least one replacement additive when the at least one additive reaches an action threshold fill level.

12. The method of claim 11, further comprising identifying, based on a single reading of sensor output, three attributes corresponding, respectively, to the pH, biocide, and corrosion inhibitor levels.

13. The method of claim 11, further comprising measuring, as a function of frequency, a lag between an applied electrical potential at the sensor and a current generated at the sensor, to obtain sensor output as a spectral response.

14. The method of claim 11, wherein the additive reservoirs comprise replaceable cartridges, the method further comprising automatically generating an indication to order a replacement additive reservoir, in response to identifying that a corresponding reservoir has reached the action threshold fill level.

15. The method of claim 11, further comprising generating a service call indication in response to identifying that sensor readings are inconsistent with normal operational parameters.

16. The device of claim 1, further comprising the controller to report to the remote location that a further action is warranted.

17. The device of claim 16, wherein the further action comprises raising an alert due to anomalous behavior.

18. The method of claim 11, further comprising determining if the cooling system is operating within a normal condition based on the threshold range.

19. The device of claim 1, further comprising the controller to identify a misconfiguration of the device based on the sensor output.

20. The method of claim 11, further comprising wherein the provisioning by automatically ordering from the remote location occurs without regard to whether the order is filled.

* * * * *